(12) United States Patent
Kojima (10) Patent No.: US 11,700,456 B2
(45) Date of Patent: Jul. 11, 2023

(54) MEDICAL CONTROL DEVICE AND MEDICAL OBSERVATION SYSTEM

(71) Applicant: Sony Olympus Medical Solutions Inc., Tokyo (JP)

(72) Inventor: Koji Kojima, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 17/478,985

(22) Filed: Sep. 20, 2021

(65) Prior Publication Data

US 2022/0166912 A1 May 26, 2022

(30) Foreign Application Priority Data

Nov. 20, 2020 (JP) ................. 2020-193777

(51) Int. Cl.
*A61B 1/06* (2006.01)
*H04N 23/72* (2023.01)
*H04N 23/56* (2023.01)
*H04N 23/667* (2023.01)
*H04N 23/50* (2023.01)

(52) U.S. Cl.
CPC ............. *H04N 23/72* (2023.01); *H04N 23/56* (2023.01); *H04N 23/667* (2023.01); *H04N 23/555* (2023.01)

(58) Field of Classification Search
CPC ............... H04N 5/2352; H04N 5/2256; H04N 5/23245; H04N 2005/2255; H04N 5/2353; H04N 5/2354; H04N 5/3532; A61B 1/00009; A61B 1/00186; A61B 1/042; A61B 1/043; A61B 1/045; A61B 1/0638; A61B 1/0655; A61B 1/0669
See application file for complete search history.

(56) References Cited

U.S. PATENT DOCUMENTS

| | | | |
|---|---|---|---|
| 2015/0022647 A1* | 1/2015 | Takei | A61B 1/00186 348/70 |
| 2017/0303768 A1* | 10/2017 | Kojima | A61B 1/0638 |
| 2019/0008372 A1* | 1/2019 | Tanaka | A61B 1/00 |
| 2020/0336653 A1* | 10/2020 | Kim | H04N 5/2351 |
| 2020/0400498 A1* | 12/2020 | Talbert | G01J 3/10 |

FOREIGN PATENT DOCUMENTS

JP 2017-60860 A 3/2017
WO WO-2022091649 A1 * 5/2022

* cited by examiner

*Primary Examiner* — Shadan E Haghani
(74) *Attorney, Agent, or Firm* — Xsensus LLP

(57) ABSTRACT

A medical control device includes: a driving mode switch configured to switch a driving mode of a rolling shutter type image sensor in which a plurality of pixels are two-dimensionally arrayed in units of horizontal lines; and a dimming controller configured to control a light emitting element configured to emit light according to a supplied current, and switch control of the light emitting element according to the driving mode.

20 Claims, 8 Drawing Sheets

MEDICAL CONTROL DEVICE AND MEDICAL OBSERVATION SYSTEM

CROSS-REFERENCE TO RELATED APPLICATION

This application claims priority from Japanese Application No. 2020-193777, filed on Nov. 20, 2020, the contents of which are incorporated by reference herein in its entirety.

BACKGROUND

The present disclosure relates to a medical control device and a medical observation system.

In the related art, there is known a medical observation system that captures an observation target in a living body or the like using an image sensor, such as a charge coupled device (CCD) and a complementary metal oxide semiconductor (CMOS), and observes the observation target (see, for example, JP 2017-60860 A).

In the medical observation system described in JP 2017-60860 A, the control of a light emitting element is switched according to a type of the CCD, the CMOS, or the like in the image sensor.

SUMMARY

Meanwhile, in a case where a CMOS image sensor is used, the entire line exposure period in which all horizontal lines in an effective pixel area in the image sensor are simultaneously exposed and a readout period for reading out charges accumulated in a plurality of pixels in the image sensor are also changed if a driving mode of the image sensor is changed. Further, in a case where the light emitting element is controlled identically in all driving modes, a stripe pattern caused by exposure unevenness sometimes occurs in a captured image thus obtained.

Therefore, there is a demand for a technique capable of suppressing generation of the stripe pattern and generating an image suitable for observation even in a case where the driving mode of the image sensor is changed.

According to one aspect of the present disclosure, there is provided a medical control device including: a driving mode switch configured to switch a driving mode of a rolling shutter type image sensor in which a plurality of pixels are two-dimensionally arrayed in units of horizontal lines; and a dimming controller configured to control a light emitting element configured to emit light according to a supplied current, and switch control of the light emitting element according to the driving mode.

DETAILED DESCRIPTION

Hereinafter, modes (hereinafter, embodiments) for carrying out the present disclosure will be described with reference to the drawings. Note that the present disclosure is not limited to the embodiments to be described below. Further, the same parts are denoted by the same reference signs when the drawings are described.

First Embodiment

Schematic Configuration of Medical Observation System

Figure 1:
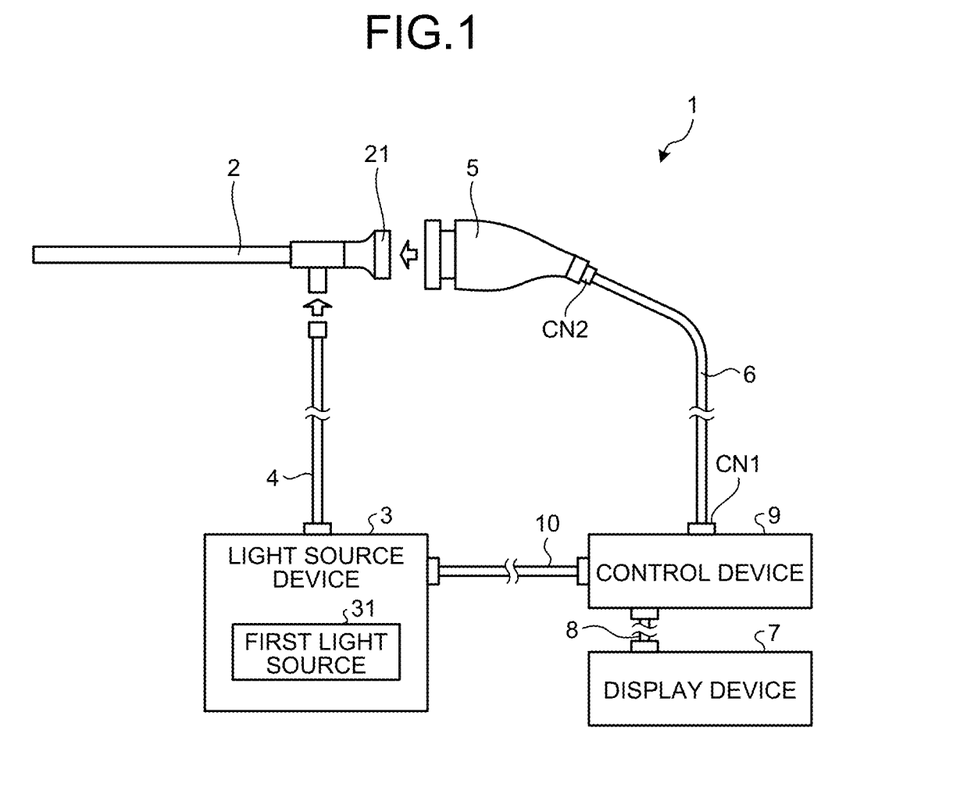
FIG. 1 is a diagram illustrating a configuration of a medical observation system according to a first embodiment.

FIG. 1 is a diagram illustrating a configuration of a medical observation system 1 according to a first embodiment.

The medical observation system 1 is a system that is used in the medical field and captures (observes) the inside of a living body (observation target) that is a subject. As illustrated in FIG. 1, the medical observation system 1 includes an insertion unit 2, a light source device 3, a light guide 4, a camera head 5, a first transmission cable 6, a display device 7, a second transmission cable 8, a control device 9, and a third transmission cable 10.

In the first embodiment, the insertion unit 2 includes a rigid endoscope. That is, the insertion unit 2 has an elongated shape that is entirely rigid or has a part that is soft and the other part that is rigid, and is inserted into the living body. An optical system, which is configured using one or a plurality of lenses and condenses light from the subject, is provided in the insertion unit 2.

The light source device 3 is connected with one end of the light guide 4, and supplies light to the one end of the light guide 4 to irradiate the inside of the living body under control of the control device 9. As illustrated in FIG. 1, the light source device 3 includes a first light source 31.

The first light source 31 corresponds to a light emitting element and a first light emitting element according to the present disclosure. The first light source 31 outputs (emits) normal light in a visible wavelength band (first wavelength band) according to a supplied current. In the first embodiment, the first light source 31 includes a light emitting diode (LED) that emits white light.

Note that the light source device 3 is configured separately from the control device 9 in the first embodiment, but the present disclosure is not limited thereto and may adopt a configuration in which the light source device 3 is provided inside the control device 9.

The one end of the light guide 4 is detachably connected to the light source device 3, and the other end thereof is detachably connected to the insertion unit 2. Further, the light guide 4 transmits light (normal light) supplied from the light source device 3 from the one end to the other end, and supplies the light to the insertion unit 2. The normal light emitted into the living body and passing through the living body (normal light reflected in the living body) is condensed by the optical system in the insertion unit 2.

The camera head 5 corresponds to an imaging device according to the present disclosure. The camera head 5 is detachably connected to a proximal end (an eyepiece portion 21 (FIG. 1)) of the insertion unit 2. Further, the camera head 5 captures the light condensed by the insertion unit 2 to generate a captured image under the control of the control device 9.

Note that a detailed configuration of the camera head 5 will be described in "Configuration of Camera Head" which will be described later.

The first transmission cable 6 has one end detachably connected to the control device 9 via a connector CN1 (FIG. 1), and the other end detachably connected to the camera head 5 via a connector CN2 (FIG. 1). Further, the first transmission cable 6 transmits the captured image and the like output from the camera head 5 to the control device 9, and transmits a control signal, a synchronization signal, a clock, power, and the like output from the control device 9 to the camera head 5.

Note that the captured image and the like may be transmitted as an optical signal or may be transmitted as an electrical signal in the transmission of the captured image and the like from the camera head 5 to the control device 9 via the first transmission cable 6. The same applies to the transmission of the control signal, the synchronization signal, and the clock from the control device 9 to the camera head 5 via the first transmission cable 6.

The display device 7 includes a display using liquid crystal, organic electro luminescence (EL), or the like, and displays an image based on a video signal from the control device 9 under the control of the control device 9.

The second transmission cable 8 has one end detachably connected to the display device 7 and the other end detachably connected to the control device 9. Further, the second transmission cable 8 transmits the video signal processed by the control device 9 to the display device 7.

The control device 9 corresponds to a medical control device according to the present disclosure. The control device 9 includes a central processing unit (CPU), a field-programmable gate array (FPGA), and the like, and integrally controls operations of the light source device 3, the camera head 5, and the display device 7.

Note that a detailed configuration of the control device 9 will be described in "Configuration of Control Device" which will be described later.

The third transmission cable 10 has one end detachably connected to the light source device 3 and the other end detachably connected to the control device 9. Further, the third transmission cable 10 transmits a control signal from the control device 9 to the light source device 3.

Configuration of Camera Head

Next, the configuration of the camera head 5 will be described.

Figure 2:
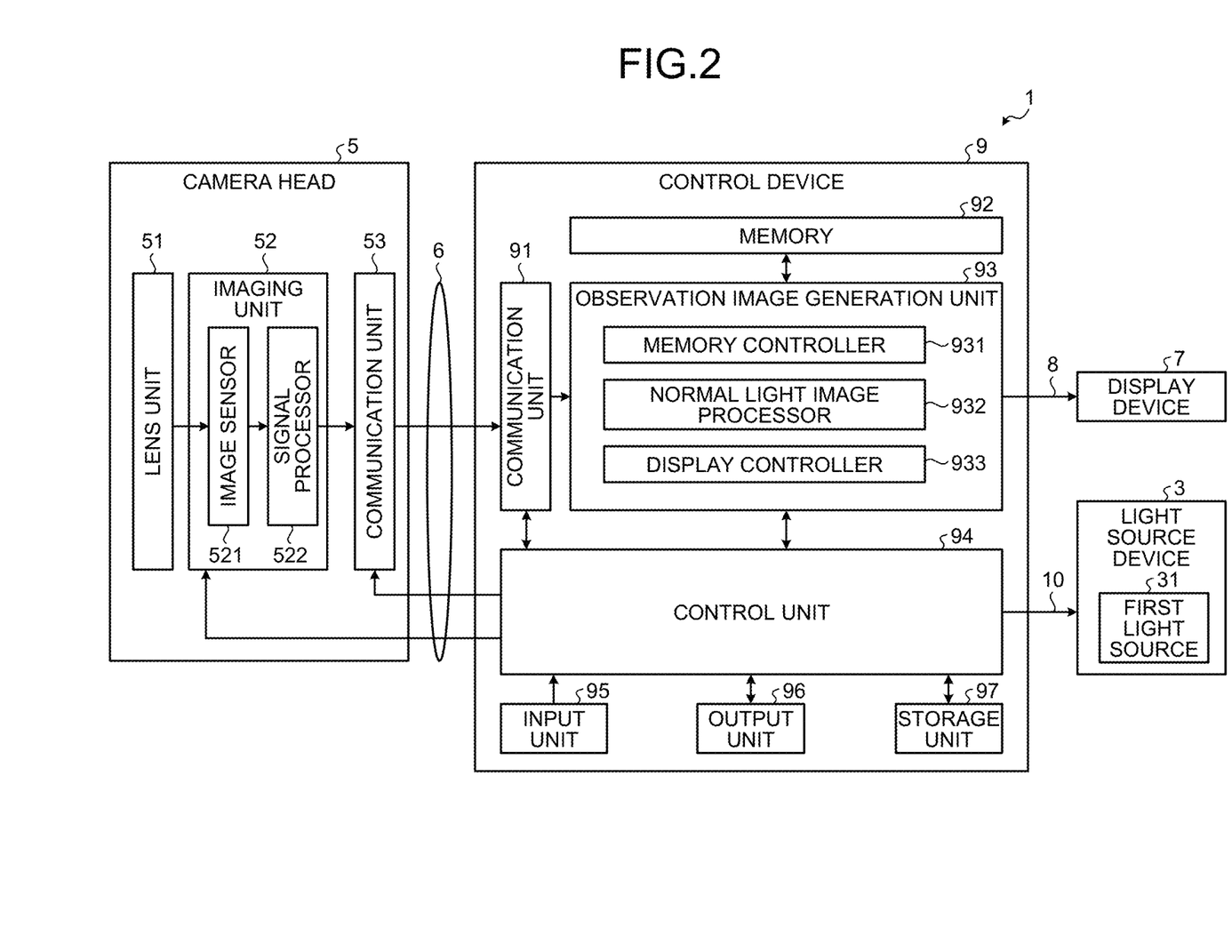
FIG. 2 is a block diagram illustrating configurations of a camera head and a control device.

FIG. 2 is a block diagram illustrating the configurations of the camera head 5 and the control device 9.

As illustrated in FIG. 2, the camera head 5 includes a lens unit 51, an imaging unit 52, and a communication unit 53.

The lens unit 51 is configured using one or a plurality of lenses, and forms an image of light (normal light) condensed by the insertion unit 2 on an imaging surface of the imaging unit 52 (image sensor 521). Note that, hereinafter, normal light (white light) directed from the lens unit 51 to the image sensor 521 will be referred to as a subject image for convenience of the description.

The imaging unit 52 captures the inside of a living body under control of the control device 9. As illustrated in FIG. 2, the imaging unit 52 includes the image sensor 521 and a signal processor 522.

The image sensor 521 receives the subject image and converts the subject image into an electrical signal (analog signal). In the first embodiment, the image sensor 521 includes a CMOS that is a rolling shutter type image sensor in which a plurality of pixels are two-dimensionally arrayed in units of horizontal lines.

Here, the image sensor 521 includes an ineffective area that is not electrically guaranteed, an optical black area (OB area), and an effective pixel area that converts a subject image formed by the lens unit 51 into an imaging signal and outputs the imaging signal although not specifically illustrated.

Hereinafter, a captured image, generated by capturing a subject image (normal light) by the image sensor 521, will be referred to as a normal light image for convenience of the description.

The signal processor 522 performs signal processing on a normal light image of an analog signal, generated by the image sensor 521, and outputs a normal light image of a digital signal.

The communication unit 53 functions as a transmitter that transmits the normal light image output from the imaging unit 52 to the control device 9 via the first transmission cable 6. The communication unit 53 includes, for example, a high-speed serial interface that performs communication of the normal light image at a transmission rate of 1 Gbps or more with the control device 9 via the first transmission cable 6.

Configuration of Control Device

Next, the configuration of the control device 9 will be described with reference to FIG. 2.

As illustrated in FIG. 2, the control device 9 includes a communication unit 91, a memory 92, an observation image generation unit 93, a control unit 94, an input unit 95, an output unit 96, and a storage unit 97.

The communication unit 91 functions as a receiver that receives a normal light image output from the camera head 5 (communication unit 53) via the first transmission cable 6. The communication unit 91 includes, for example, a high-speed serial interface that performs communication of the normal light image with the communication unit 53 at a transmission rate of 1 Gbps or more.

The memory 92 includes, for example, a dynamic random access memory (DRAM) or the like. The memory 92 may temporarily store a plurality of frames of normal light images sequentially output from the camera head 5 (communication unit 53).

The observation image generation unit 93 processes the normal light images sequentially output from the camera head 5 (communication unit 53) and received by the communication unit 91 under control of the control unit 94. As illustrated in FIG. 2, the observation image generation unit 93 includes a memory controller 931, a normal light image processor 932, and a display controller 933.

The memory controller 931 controls write and readout of the normal light image to and from the memory 92. More specifically, the memory controller 931 sequentially writes the normal light images, sequentially output from the camera head 5 (communication unit 53) and received by the communication unit 91, to the memory 92. In addition, the memory controller 931 reads out a normal light image from the memory 92 at a specific timing, and inputs the readout normal light image to the normal light image processor 932.

The normal light image processor 932 executes first image processing on the input normal light image.

Examples of the first image processing may include optical black subtraction processing, white balance adjustment processing, demosaic processing, and color correction matrix processing, gamma correction processing, and YC processing for converting an RGB signal (normal light image) into a luminance/color difference signal (Y, Cb/Cr signal).

The display controller 933 generates a video signal for displaying the normal light image after the first image processing is executed by the normal light image processor 932 under the control of the control unit 94. Further, the display controller 933 outputs the video signal to the display device 7 via the second transmission cable 8.

The control unit 94 is configured using, for example, a CPU, an FPGA, or the like, and outputs a control signal via the first to third transmission cables 6, 8, and 10, thereby controlling the operations of the light source device 3, the camera head 5, and the display device 7 and controlling the overall operation of the control device 9. The control unit 94 has functions as a driving mode switching unit and a dimming controller according to the present disclosure. Note that functions of the driving mode switching unit and the dimming controller will be described in "Operation of Control Device" which will be described later.

The input unit 95 is configured using an operation device such as a mouse, a keyboard, and a touch panel, and receives a user operation from a user such as a doctor. Further, the input unit 95 outputs an operation signal corresponding to the user operation to the control unit 94.

The output unit 96 is configured using a speaker, a printer, or the like, and outputs various types of information.

The storage unit 97 stores a program executed by the control unit 94, information necessary for processing of the control unit 94, and the like.

Operation of Control Device

Next, the operation of the control device 9 will be described.

Note that, hereinafter, the function of the driving mode switching unit in the control unit 94 and the function of the dimming controller in the control unit 94 will be mainly described for convenience of the description.

The control unit 94 controls the image sensor 521 as follows.

Specifically, the control unit 94 performs exposure control according to a so-called rolling shutter scheme in which exposure of the image sensor 521 in one field period is started sequentially for each horizontal line and readout is performed sequentially for each horizontal line for which a predetermined period (so-called shutter speed) has elapsed from the start of exposure.

Further, the control unit 94 (driving mode switching unit) switches a control pattern (driving mode) of the exposure control described above. In the first embodiment, the control unit 94 (driving mode switching unit) switches the driving mode to any of first to third driving modes in accordance with, for example, a user operation on the input unit 95 performed by a user such as an operator.

Note that details of the first to third driving modes will be described later.

In addition, the control unit 94 (dimming controller) executes dimming control for adjusting a normal light image to have reference brightness based on brightness (an average value of luminance values or the like) of a specific area (detection area) in the normal light image. In the first embodiment, the control unit 94 may execute, as the dimming control, first control for adjusting a supply time of a current to be supplied to the first light source 31 (an applied pulse width of the current), second control for adjusting a current value to be supplied to the first light source 31, and third control for adjusting an electronic shutter of the image sensor 521. Further, the control unit 94 switches the dimming control according to the driving mode of the image sensor 521.

Hereinafter, the dimming control in the first driving mode, the dimming control in the second driving mode, and the dimming control in the third driving mode will be described in order.

Dimming Control in First Driving Mode

Figure 3:
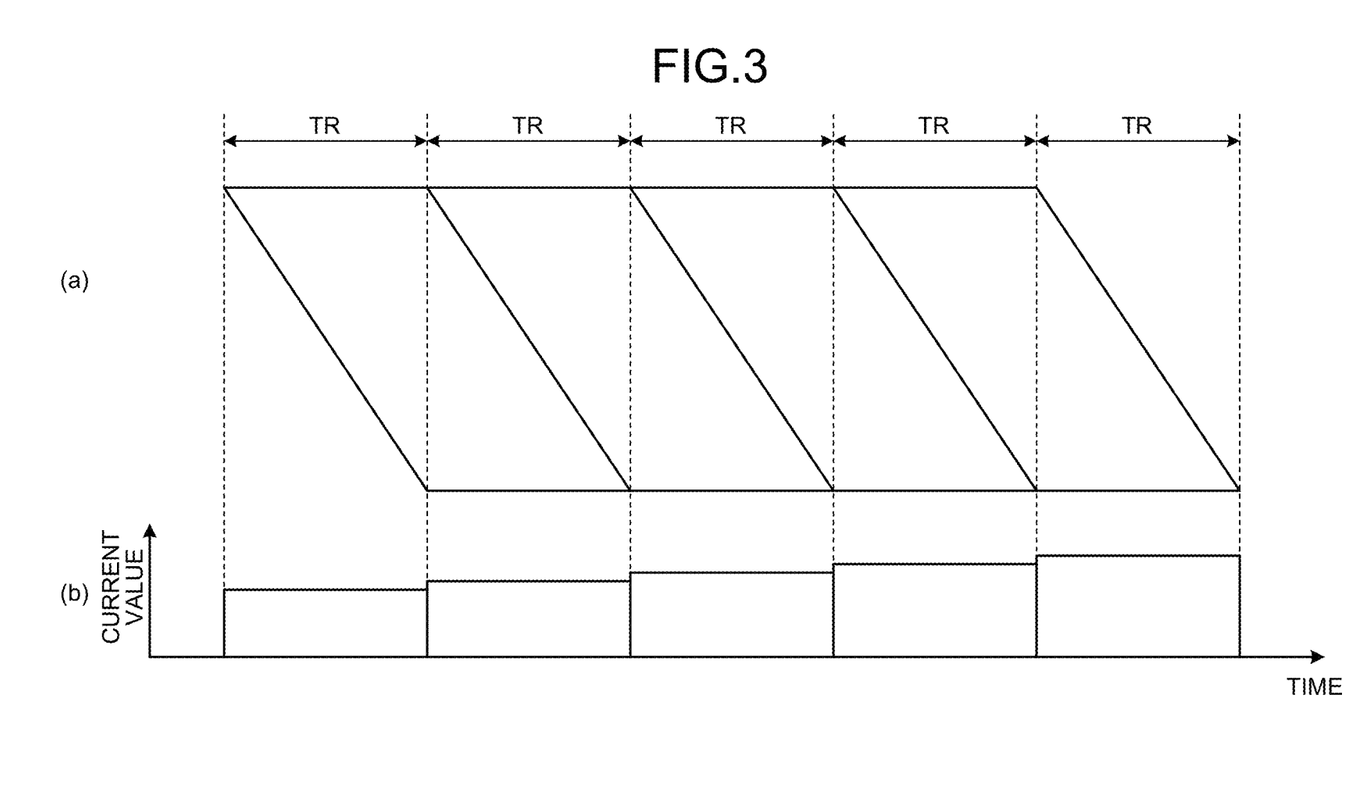
FIG. 3 is a view for describing dimming control in a first driving mode.
Figure 4:
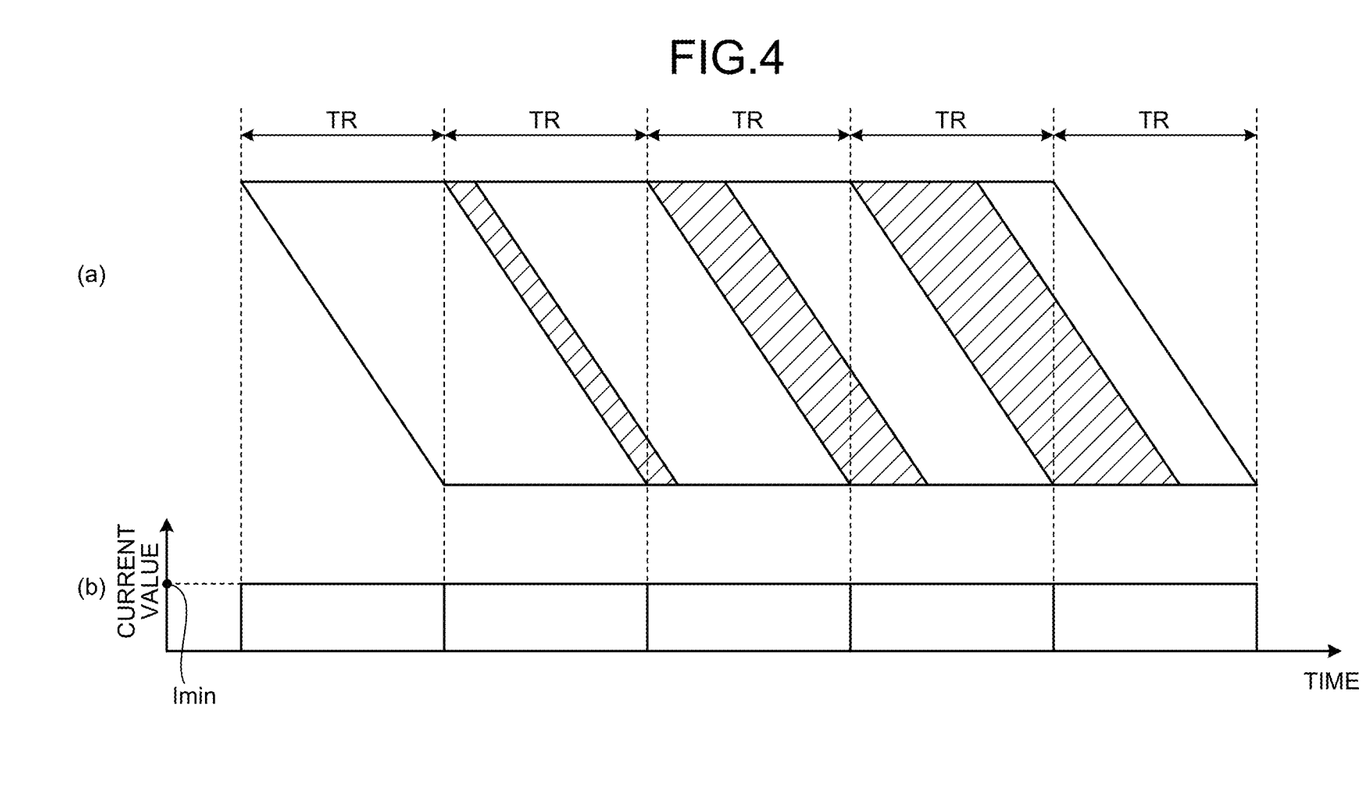
FIG. 4 is a view for describing the dimming control in the first driving mode.

FIGS. 3 and 4 are views for describing the dimming control in the first driving mode. Specifically, FIGS. 3(a) and 4(a) are views illustrating exposure timings of the image sensor 521, where the vertical axis represents the horizontal line of the image sensor 521 (the uppermost line indicates the uppermost horizontal line (the first horizontal line), and the lowermost line indicates the lowermost horizontal line (the last line)), and the horizontal axis represents time. Further, a parallelogram area is an area that contributes to generation of a normal light image of one field. FIGS. 3(b) and 4(b) are views illustrating dimming control, where the vertical axis represents a current value to be supplied to the first light source 31, and the horizontal axis represents time (supply time of a current to be supplied to the first light source 31). Note that the third control (adjustment of the electronic shutter) in the dimming control is indicated by hatching in FIGS. 3(b) and 4(b). In addition, FIG. 3 illustrates a case where the brightness of a normal light image is increased by the dimming control, and FIG. 4 illustrates a case where the brightness of a normal light image is decreased by the dimming control.

As illustrated in FIGS. 3(a) and 4(a), the first driving mode is a driving mode in which a readout period TR for reading out charges accumulated in a plurality of pixels of the image sensor 521 is long, and the entire line exposure period is not acquirable. Here, the entire line exposure period is a period in which all the horizontal lines in the effective pixel area in the image sensor 521 are simultaneously exposed.

Further, when the driving mode of the image sensor 521 is the first driving mode, the control unit 94 (dimming controller) executes dimming control to be described hereinafter.

First, a case where the brightness of a normal light image is increased by the dimming control is assumed.

In this case, as illustrated in FIG. 3(b), the control unit 94 (dimming controller) fixes a supply time of a current to be supplied to the first light source 31 (the supply time: one field) for each field, and increases a current value supplied to the first light source 31 by the second control while fixing the electronic shutter of the image sensor 521 (in the NTSC scheme: 1/60 [sec]) to increase the brightness of the normal light image.

Next, a case where the brightness of a normal light image is decreased by the dimming control is assumed.

In this case, as illustrated in FIG. 4(b), the control unit 94 (dimming controller) fixes a supply time of a current to be supplied to the first light source 31 (the supply time: one field) for each field, and adjusts the electronic shutter by the third control while fixing a current value supplied to the first light source 31 at a minimum rated current value Imin to decrease the brightness of the normal light image.

Note that a parallelogram indicated by hatching is an area indicating sweeping of charges by the electronic shutter in FIG. 4(b). In addition, a parallelogram area indicated by an outline is an area indicating an effective exposure period.

As described above, when the driving mode of the image sensor 521 is the first driving mode, the control unit 94

(dimming controller) executes only the second control and third control among the first control to third control as the dimming control.

Dimming Control in Second Driving Mode

Figure 5:
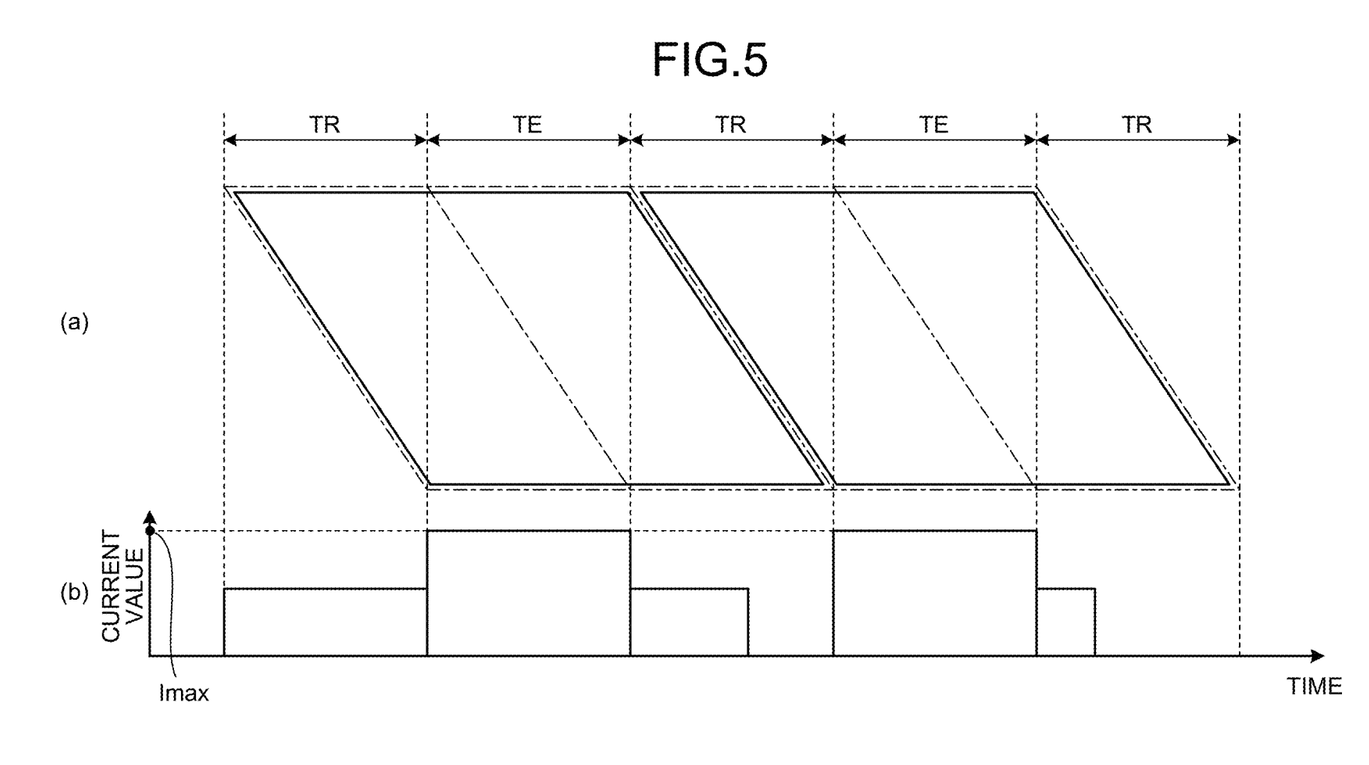
FIG. 5 is a view for describing dimming control in a second driving mode.

FIG. 5 is a view for describing the dimming control in the second driving mode. Specifically, FIG. 5 is the view corresponding to FIGS. 3 and 4.

Here, a case where a readout period is long and the entire line exposure period is not acquirable is assumed as indicated by an alternate long and short dash line in FIG. 5(a).

The second driving mode is a driving mode called long-time exposure or long-second exposure in which a plurality of (two in the example of FIG. 5(a)) fields are combined to one field in a pseudo manner. That is, if the driving mode of the image sensor 521 is switched from a driving mode indicated by the alternate long and short dash line in FIG. 5(a) to the second driving mode, an entire line exposure period TE is generated in a pseudo manner per field combined in a pseudo manner as indicated by the solid line in FIG. 5(a).

Further, when the driving mode of the image sensor 521 is the second driving mode, the control unit 94 (dimming controller) executes dimming control to be described hereinafter.

As illustrated in FIG. 5(b), the control unit 94 (dimming controller) sets a current value supplied to the first light source 31 to a maximum rated current value Imax for the entire line exposure period TE generated in a pseudo manner by the second driving mode while fixing the electronic shutter of the image sensor 521 per field combined in a pseudo manner. Further, the control unit 94 (dimming controller) adjusts a supply time of a current supplied to the first light source 31 by the first control during the readout period TR generated in a pseudo manner by the second driving mode per field combined in a pseudo manner, thereby adjusting the brightness of a normal light image.

Here, a light emission amount of the first light source 31 during the entire line exposure period TE (current value supplied to the first light source 31×current supply time) is higher than a light emission amount of the first light source 31 during the readout period TR.

As described above, when the driving mode of the image sensor 521 is the second driving mode, the control unit 94 (dimming controller) executes only the first control and second control among the first control to third control as the dimming control.

Dimming Control in Third Driving Mode

Figure 6:
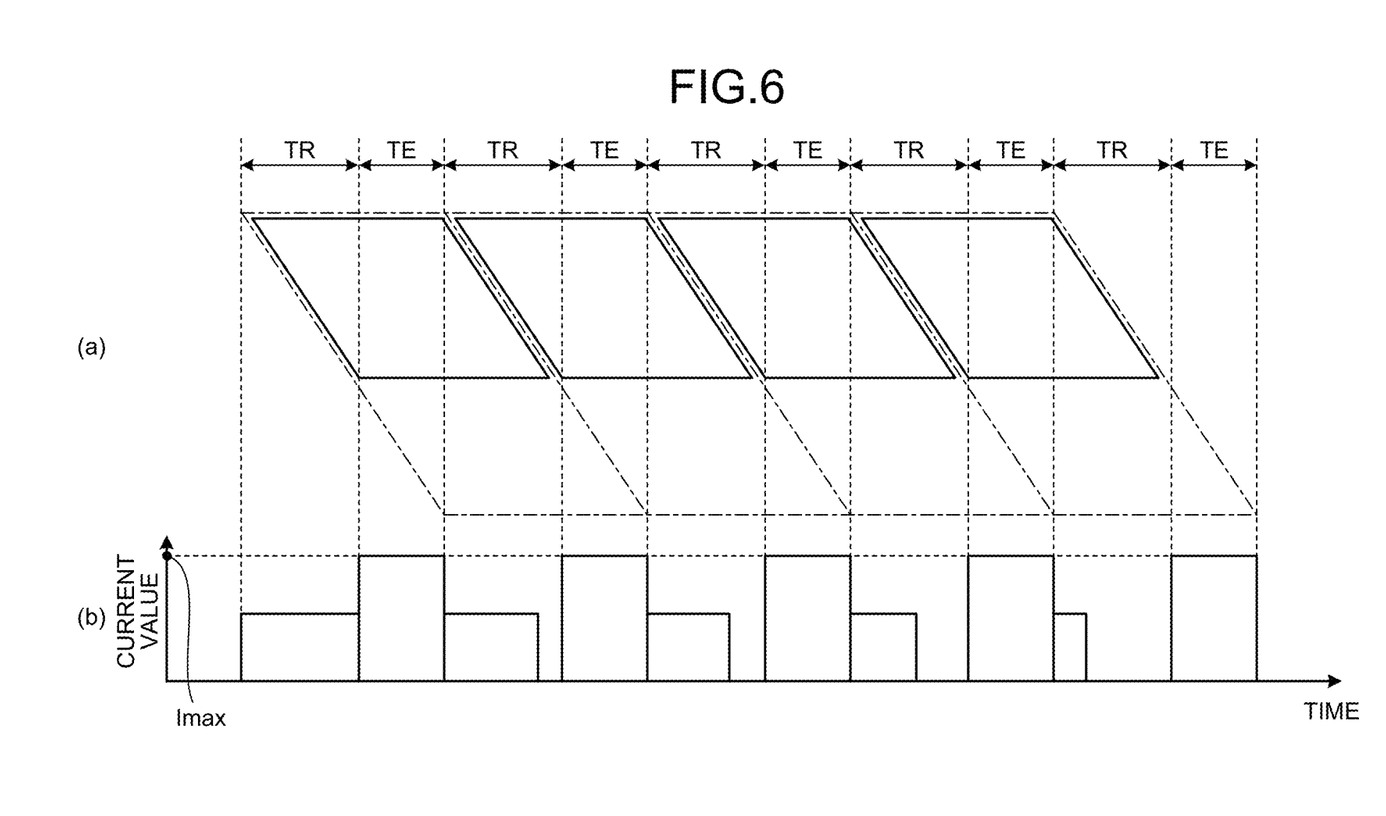
FIG. 6 is a view for describing dimming control in a third driving mode.

FIG. 6 is a view for describing the dimming control in the third driving mode. Specifically, FIG. 6 is the view corresponding to FIGS. 3 to 5. A case where a readout period is long and the entire line exposure period is not acquirable is assumed here as indicated by an alternate long and short dash line in FIG. 6(a).

The third driving mode is a driving mode including binning. The binning is not limited to adding adjacent pixels, but includes performing readout while thinning out some pixels. That is, if the driving mode of the image sensor 521 is switched from a driving mode indicated by the alternate long and short dash line in FIG. 6(a) to the third driving mode, the readout speed may be increased, and the entire line exposure period TE is generated in a pseudo manner per field as indicated by the solid line in FIG. 6(a).

Further, when the driving mode of the image sensor 521 is the third driving mode, the control unit 94 (dimming controller) executes dimming control to be described hereinafter.

As illustrated in FIG. 6(b), the control unit 94 (dimming controller) sets a current value supplied to the first light source 31 to a maximum rated current value Imax for the entire line exposure periods TE generated in a pseudo manner by the third driving mode while fixing the electronic shutter of the image sensor 521 per field. Further, the control unit 94 (dimming controller) adjusts a supply time of a current supplied to the first light source 31 by the first control during the readout period TR generated in a pseudo manner by the third driving mode per field, thereby adjusting the brightness of a normal light image.

Here, a light emission amount of the first light source 31 during the entire line exposure period TE (current value supplied to the first light source 31×current supply time) is higher than a light emission amount of the first light source 31 during the readout period TR.

As described above, when the driving mode of the image sensor 521 is the third driving mode, the control unit 94 (dimming controller) executes only the first control and second control among the first control to third control as the dimming control.

According to the first embodiment described above, the following effects are achieved.

The control device 9 according to the first embodiment switches the first control to third control (dimming control) according to the driving mode of the image sensor 521.

Specifically, when the driving mode of the image sensor 521 is the first driving mode, the control device 9 executes only the second control and third control among the first control to third control as the dimming control.

Here, the second control is executed in the case of increasing the brightness of the normal light image. That is, a luminance difference between an upper position and a lower position in the normal light image increases according to an increase in the light emission amount (current value supplied to first light source 31×current supply time) between adjacent fields. In other words, the luminance difference in the normal light image may be suppressed by reducing the increase in the light emission amount between the adjacent fields. In addition, the electronic shutter of the image sensor 521 is adjusted while fixing the light emission amount of the first light source 31 in the case of decreasing the brightness of the normal light image. That is, no luminance difference occurs in the normal light image since all the lines of the image sensor 521 sweep out charges of the same time by the electronic shutter.

In addition, when the driving mode of the image sensor 521 is the second or third driving mode, the control device 9 executes only the first control and second control among the first control to third control as the dimming control.

Here, the control device 9 sets the current value supplied to the first light source 31 to the maximum rated current value Imax for the entire line exposure periods TE generated in a pseudo manner, and executes the first control in the readout period TR generated in a pseudo manner. That is, the luminance difference in the normal light image by the first control in the readout period TR may be made inconspicuous by causing the first light source 31 to fully emit light in the entire line exposure period TE.

Accordingly, it is possible to suppress the luminance difference in the normal light image even in a case where the driving mode of the image sensor 521 is changed, and to generate the normal light image suitable for observation.

Second Embodiment

Next, a second embodiment will be described.

In the following description, the same reference signs are given to the same configurations as those of the above-described first embodiment, and a detailed description thereof will be omitted or simplified.

Figure 7:
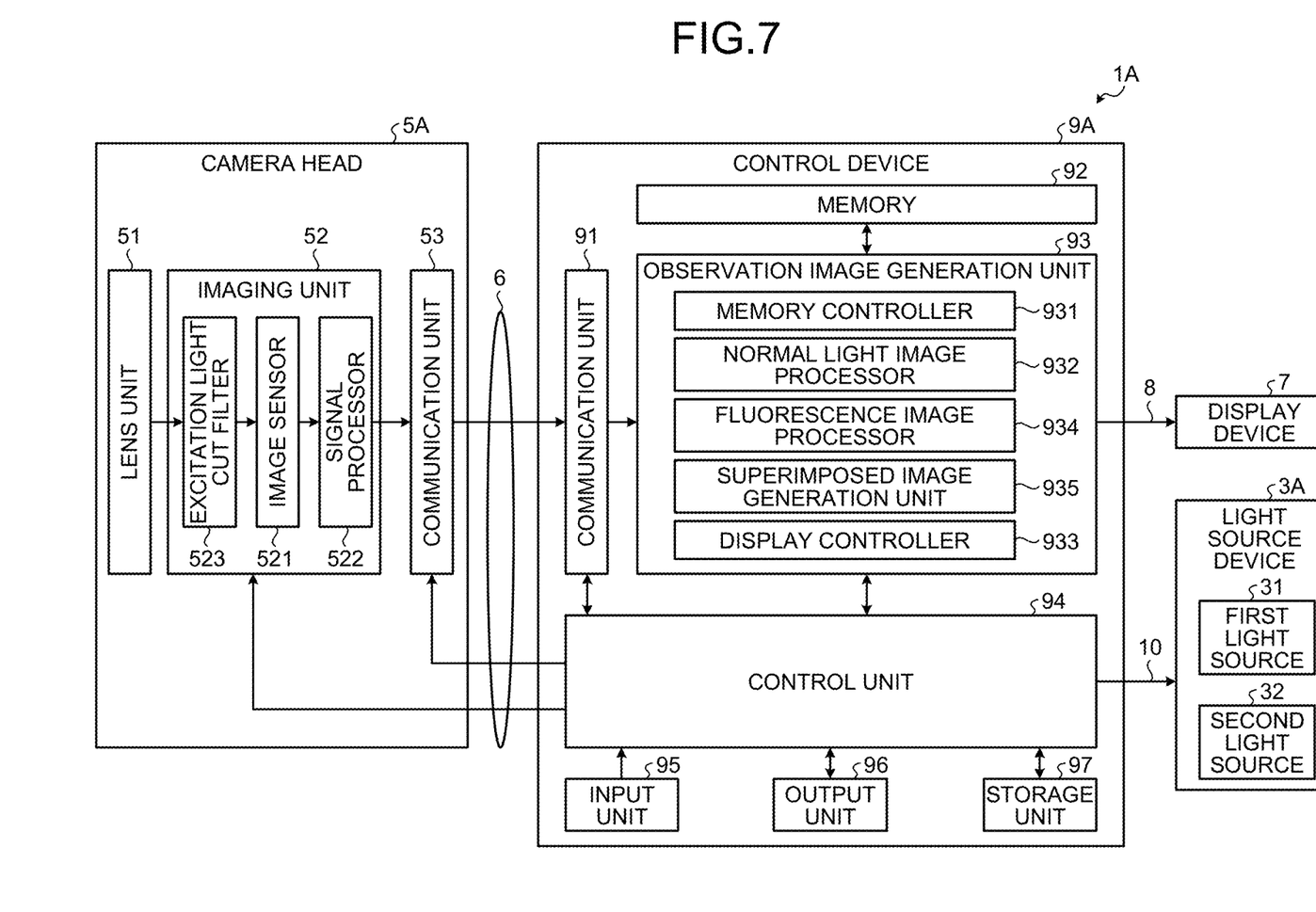
FIG. 7 is a diagram illustrating a configuration of a medical observation system according to a second embodiment.

FIG. 7 is a diagram illustrating a configuration of a medical observation system 1A according to the second embodiment.

In the medical observation system 1A according to the second embodiment, a first observation mode and a second observation mode may be executed.

The first observation mode is an observation mode in which the inside of a living body irradiated with normal light is captured by the image sensor 521 to obtain a normal light image (first captured image) similarly to the medical observation system 1 of the first embodiment described above.

The second observation mode is an observation mode in which a normal light image is obtained and the inside of the living body irradiated with light in a second wavelength band, which is a wavelength band different from that of the normal light, is captured by the image sensor 521 to obtain a second captured image (hereinafter, referred to as a fluorescence image).

Further, as illustrated in FIG. 7, configurations of the light source device 3, the camera head 5, and the control device 9 in the medical observation system 1A are changed from those of the medical observation system 1 described in the first embodiment described above. Hereinafter, the light source device 3, the camera head 5, and the control device 9 according to the second embodiment will be referred to as a light source device 3A, a camera head 5A, and a control device 9A for convenience of the description.

In the light source device 3A, a second light source 32 is added to the light source device 3, described in the above-described first embodiment, as illustrated in FIG. 7.

The second light source 32 corresponds to a light emitting element and a second light emitting element according to the present disclosure. The second light source 32 includes a semiconductor laser or an LED that emits near-infrared excitation light in a near-infrared wavelength band which is the second wavelength band (for example, a wavelength band of about 750 nm to 800 nm). The near-infrared excitation light is excitation light that excites a fluorescent substance such as indocyanine green. In addition, when being excited by the near-infrared excitation light, the fluorescent substance, such as indocyanine green, emits fluorescence in a wavelength band (for example, a wavelength band around 830 nm), other than the visible range, which has a central wavelength on the longer wavelength side than a central wavelength of the wavelength band of the near-infrared excitation light. Note that the wavelength band of the near-infrared excitation light and the wavelength band of the fluorescence may be set so as to partially overlap each other, or may be set so as not to overlap each other at all.

Further, only the first light source 31 is driven in the first observation mode under control of the control device 9A in the light source device 3A according to the second embodiment as illustrated in FIGS. 3 to 6 in the above-described first embodiment.

In addition, the first light source 31 is driven during a first period between alternately repeated first and second periods under the control of the control device 9A in the second observation mode in the light source device 3A according to the second embodiment. That is, the light source device 3 emits normal light (white light) during the first period. In addition, the second light source 32 is driven during the second period under the control of the control device 9A in the light source device 3A. That is, the light source device 3A emits near-infrared excitation light during the second period. Further, when the inside of a living body is irradiated with the near-infrared excitation light via the light guide 4 and the insertion unit 2, the near-infrared excitation light passing through the living body (near-infrared excitation light reflected in the living body) and fluorescence emitted from a fluorescent substance as the fluorescent substance, such as indocyanine green, accumulated at a lesion in the living body is excited by the near-infrared excitation light, are condensed by an optical system in the insertion unit 2.

As illustrated in FIG. 7, an excitation light cut filter 523 is added to the imaging unit 52 in the camera head 5A as compared with the camera head 5 described in the above-described first embodiment.

The excitation light cut filter 523 is provided between the lens unit 51 and the image sensor 521, and includes a band stop filter that removes a specific wavelength band. Note that, hereinafter, a wavelength band to be cut (removed) by the excitation light cut filter 523 will be referred to as a cut band, a wavelength band that is closer to a short wavelength side than the cut band and is transmitted through the excitation light cut filter 523 will be referred to as a short-wavelength-side transmission area, and a wavelength band that is closer to a long wavelength side than the cut band and is transmitted through the excitation light cut filter 523 will be referred to as a long-wavelength-side transmission area, for convenience of the description.

Here, the cut band includes at least a part of the wavelength band of near-infrared excitation light. In the first embodiment, the cut band includes the entire wavelength band of the near-infrared excitation light. In addition, the long-wavelength-side transmission area includes the wavelength band of fluorescence. Further, the short-wavelength-side transmission area includes the wavelength band of normal light (white light).

That is, the excitation light cut filter 523 transmits a subject image (normal light) directed from the lens unit 51 to the image sensor 521. On the other hand, the excitation light cut filter 523 removes near-infrared excitation light and transmits fluorescence for the near-infrared excitation light and fluorescence directed from the lens unit 51 to the image sensor 521. Note that, hereinafter, the fluorescence that is transmitted through the excitation light cut filter 523 and directed to the image sensor 521 will be referred to as a fluorescent image for convenience of the description.

Further, the image sensor 521 captures the subject image to generate a normal light image, and captures the fluorescent image to generate a fluorescence image.

As illustrated in FIG. 7, a fluorescence image processor 934 and a superimposed image generation unit 935 are added to the observation image generation unit 93 in the control device 9A as compared with the control device 9A described in the above-described first embodiment.

Here, the memory controller 931 operates in the same manner as the operation described in the first embodiment in the first observation mode.

In addition, the memory controller 931 operates as follows in the second observation mode.

The memory controller 931 sequentially writes captured images (the normal light image and the fluorescence image), sequentially output from the camera head 5A (communication unit 53) and received by the communication unit 91, into the memory 92. In addition, the memory controller 931 reads out a normal light image from the memory 92 at a specific timing, and inputs the readout normal light image to the normal light image processor 932. Further, the memory controller 931 reads out the fluorescence image from the memory 92 at a specific timing, and inputs the read fluorescence image to the fluorescence image processor 934.

In the second observation mode, the fluorescence image processor 934 executes second image processing different from first image processing, executed by the normal light image processor 932, on the input fluorescence image.

Examples of the second image processing may include optical black subtraction processing, white balance adjustment processing, demosaic processing, and color correction matrix processing, gamma correction processing, and YC processing for converting an RGB signal (fluorescence image) into a luminance/color difference signal (Y, Cb/Cr signal), which is similar to the first image processing.

In the second observation mode, the superimposed image generation unit 935 executes superimposition processing for superimposing the fluorescence image on which the second image processing has been executed by the fluorescence image processor 934 on the normal light image on which the first image processing has been executed by the normal light image processor 932 to generate a superimposed image.

Here, as the superimposition processing, first and second superimposition processes to be described below may be exemplified. Note that, hereinafter, an area, which includes a pixel whose luminance value is a specific threshold or more, in a fluorescence image will be referred to as a fluorescence area.

The first superimposition process is a process of replacing an area at the same pixel position as a fluorescence area in a normal light image with an image of the fluorescence area in a fluorescence image.

The second superimposition process is a process (so-called alpha blend process) of changing brightness of a color indicating fluorescence applied to each pixel in an area at the same pixel position as a fluorescence area in a normal light image according to a luminance value at each pixel position in the fluorescence area of a fluorescence image.

Further, the display controller 933 generates a video signal for displaying the normal light image on which the first image processing has been executed by the normal light image processor 932 in the first observation mode as described in the above-described first embodiment.

In addition, the display controller 933 generates a video signal for displaying the superimposed image generated by the superimposed image generation unit 935 in the second observation mode.

In addition, the control unit 94 according to the second embodiment has a function as an observation mode switching unit in addition to functions as a driving mode switching unit and a dimming controller according to the present disclosure.

Next, the operation of the control device 9A will be described.

Note that, hereinafter, the function of the driving mode switching unit in the control unit 94, the function of the dimming controller in the control unit 94, and the function of the observation mode switching unit in the control unit 94 will be mainly described for convenience of the description.

For example, the control unit 94 (observation mode switching unit) switches an observation mode to any of the first and second observation modes in accordance with a user operation on the input unit 95 performed by a user such as an operator.

In the first observation mode, the control unit 94 (driving mode switching unit and dimming controller) operates similarly to the operation described in "Dimming Control in First Driving Mode", "Dimming Control in Second Driving Mode", and "Dimming Control in Third Driving Mode" in the first embodiment described above. Therefore, only functions of the control unit 94 (driving mode switching unit and dimming controller) in the second observation mode will be described hereinafter.

Figure 8:
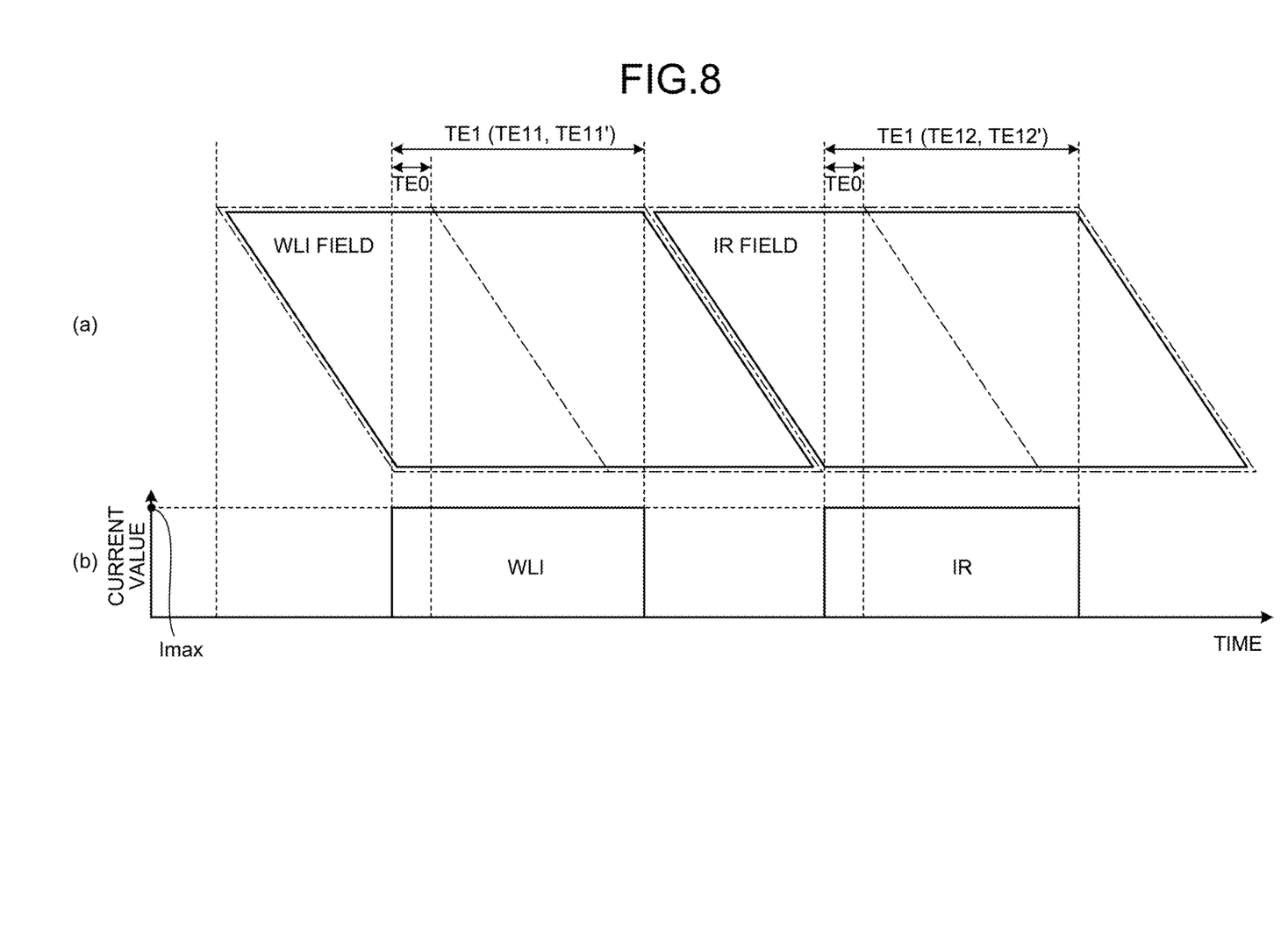
FIG. 8 is a view for describing functions of a control unit (a driving mode switching unit and a dimming controller) in a second observation mode.

FIG. 8 is a view for describing the functions of the control unit 94 (driving mode switching unit and dimming controller) in the second observation mode. Specifically, FIG. 8 is the view corresponding to FIGS. 3 to 6. Here, the alternate long and short dash line illustrated in FIG. 8(a) indicates a driving mode before switching. In addition, the solid line illustrated in FIG. 8(b) indicates a driving mode (second driving mode) after the switching.

Here, a case where a readout period is long and an entire line exposure period TE0 is short is assumed as indicated by the alternate long and short dash line in FIG. 8(a).

In this case, when the observation mode is switched to the second observation mode, the control unit 94 (driving mode switching unit) switches the driving mode of the image sensor 521 to the second driving mode. Further, if the driving mode of the image sensor 521 is switched from the driving mode indicated by the alternate long and short dash line in FIG. 8(a) to the second driving mode, an entire line exposure period TE1, longer than the entire line exposure period TE0, is generated in a pseudo manner per field combined in a pseudo manner as indicated by the solid line in FIG. 8(a).

Thereafter, the control unit 94 (dimming controller) alternately repeats light emission of the first light source 31 and light emission of the second light source 32 per field combined in a pseudo manner as illustrated in FIG. 8(b). Note that, in FIG. 8(a), an area of a solid parallelogram contributing to generation of a normal light image is described as a white light imaging (WLI) field, and an area of a solid parallelogram contributing to generation of a fluorescence image is described as an infra-red (IR) field, among the respective fields combined into one field in a pseudo manner. In addition, in FIG. 8(b), emission of normal light is described as WLI, and emission of excitation light is described as IR.

Specifically, in the WLI field between the alternately repeated WLI field and IR field, the control unit 94 (dimming controller) causes the first light source 31 to emit light during a whole first period TE11' within an entire line exposure period TE11 generated in a pseudo manner by the second driving mode. Note that FIG. 8(b) illustrates a case where a current supply time is maximized and a current value is set to the maximum rated current value Imax. Therefore, the first period TE11' is the same period as the entire line exposure period TE11.

On the other hand, in the IR field between the alternately repeated WLI field and IR field, the control unit 94 (dimming controller) causes the second light source 32 to emit light in a whole second period TE12' within an entire line exposure period TE12 generated in a pseudo manner by the second driving mode. Note that FIG. 8(b) illustrates a case where a current supply time is maximized and a current value is set to the maximum rated current value Imax. Therefore, the second period TE12' is the same period as the entire line exposure period TE12.

According to the second embodiment described above, not only the same effects as those in the above-described first embodiment but also the following effects are obtained.

When the observation mode is the second observation mode, the control device 9A according to the second embodiment switches the driving mode of the image sensor 521 to the second driving mode. In addition, the control device 9A causes the first and second light sources 31 and 32 to emit light every entire line exposure period TE generated in a pseudo manner in the second driving mode.

That is, the brightness of a normal light image and a fluorescence image is insufficient in a configuration in which the first and second light sources 31 and 32 emit light every entire line exposure period TE0. However, it is possible to sufficiently secure the brightness of the normal light image and the fluorescence image by generating the entire line exposure period TE1 longer than the entire line exposure period TE0 in a pseudo manner and causing the first and second light sources 31 and 32 to emit light every entire line exposure periods TE1. Therefore, an image suitable for observation may be generated.

Other Embodiments

The modes for carrying out the present disclosure have been described hereinbefore. However, the present disclosure is not limited only to the first and second embodiments described above.

Although the function of adjusting the electronic shutter of the image sensor 521 is included as the function of the dimming controller according to the present disclosure in the first and second embodiments described above, the present disclosure is not limited thereto, and a function of controlling only the first light source 31 (second light source 32) may be provided.

Although the number of the driving modes of the image sensor 521 is three in the first and second embodiments described above, the present disclosure is not limited thereto, and only two driving modes may be used, or four or more driving modes may be used.

Although the light source control device according to the present disclosure is mounted on the medical observation system 1 in which the insertion unit 2 is configured using the rigid endoscope in the first and second embodiments described above, the present disclosure is not limited thereto. For example, the light source control device according to the present disclosure may be mounted on a medical observation system in which the insertion unit 2 is configured using a flexible endoscope. In addition, the light source control device according to the present disclosure may be mounted on a medical observation system such as a surgical microscope (see, for example, JP 2016-42981 A) that enlarges and observes a predetermined visual field area in a subject (in a living body) or a subject surface (living body surface).

A part of the configuration of the camera head 5 or a part of the configuration of the control device 9 may be provided in, for example, the connector CN1 or the connector CN2 in the first and second embodiments described above.

Meanwhile, photo-dynamic diagnosis (PDD), which is one of cancer diagnosis methods for detecting a cancer cell, is known.

In the photodynamic diagnosis, for example, a photosensitive substance such as 5-aminolevulinic acid (hereinafter, referred to as 5-ALA) is used. The 5-ALA is a natural amino acid originally contained in living organisms of animals and plants. This 5-ALA is taken into a cell after administration in vivo, and is biosynthesized into protoporphyrin in mitochondria. Further, the protoporphyrin is excessively accumulated in a cancer cell. In addition, the protoporphyrin excessively accumulated in the cancer cell has photoactivity. Therefore, the protoporphyrin emits fluorescence (for example, red fluorescence in a wavelength band of 600 nm to 740 nm) when being excited with excitation light (for example, blue visible light in a wavelength band of 375 nm to 445 nm). In this manner, a cancer diagnostic method in which a cancer cell is caused to emit fluorescence using a photosensitizer is referred to as the photo-dynamic diagnosis.

Further, the first light source 31 may be configured using an LED that emits white light and the second light source 32 may be configured using a semiconductor laser that emits excitation light for exciting protoporphyrin (for example, blue visible light in a wavelength band of 375 nm to 445 nm) in the second embodiment. Even in the case of adopting such a configuration, the same effects as those of the second embodiment described above are obtained.

Although the first and second periods are set to be alternately repeated in the second observation mode in the second embodiment described above, the present disclosure is not limited thereto, and at least one of the first and second periods may be continuous such that a frequency ratio between the first and second periods is a ratio other than 1:1.

Note that the following configuration also belongs to the technical scope of the present disclosure.

(1) A medical control device including: a driving mode switching unit that switches a driving mode of a rolling shutter type image sensor in which a plurality of pixels are two-dimensionally arrayed in units of horizontal lines; and a dimming controller that controls a light emitting element which emits light according to a supplied current, and the dimming controller switches control of the light emitting element according to the driving mode.

(2) The medical control device according to (1), in which the dimming controller is capable of executing dimming control including first control for adjusting a supply time of a current to be supplied to the light emitting element, second control for adjusting a current value to be supplied to the light emitting element, and third control for adjusting an electronic shutter of the image sensor, and switches the dimming control according to the driving mode.

(3) The medical control device according to (2), in which the dimming controller executes only the second control and the third control among the first control, the second control, and the third control when the driving mode is a first driving mode in which there is no entire line exposure period in which all horizontal lines in an effective pixel area in the image sensor are simultaneously exposed.

(4) The medical control device according to (2) or (3), in which the dimming controller executes only the first control and the second control among the first control, the second control, and the third control when the driving mode is a second driving mode of long-time exposure in which a plurality of fields are combined to one field in a pseudo manner.

(5) The medical control device according to (4), in which the dimming controller sets a light emission amount of the light emitting element in an entire line exposure period in which all lines of an effective pixel area in the image sensor are simultaneously exposed to be higher than a light emission amount of the light emitting element in another period when the driving mode is the second driving mode, the entire line exposure period being a period generated in a pseudo manner by the second driving mode.

(6) The medical control device according to any one of (2) to (5), in which the dimming controller executes only the first control and the second control among the first control, the second control, and the third control when the driving mode is a third driving mode including binning.

(7) The medical control device according to (6), in which when the driving mode is the third driving mode, the dimming controller sets a light emission amount of the light emitting element in an entire line exposure period in which all lines of an effective pixel area in the image sensor are simultaneously exposed to be higher than a light emission amount of the light emitting element in another period, the entire line exposure period being a period generated in a pseudo manner by the third driving mode.

(8) The medical control device according to any one of (1) to (7), in which the light emitting element includes a first light emitting element which emits light in a first wavelength band, and a second light emitting element which emits light in a second wavelength band different from the first wavelength band, the medical control device further includes an observation mode switching unit that switches an observation mode to a first observation mode or a second observation mode, the first observation mode is an observation mode in which an observation target irradiated with the light in the first wavelength band is captured by the image sensor to obtain a first captured image, the second observation mode is an observation mode in which the first captured image is obtained and the observation target irradiated with the light in the second wavelength band is captured by the image sensor to obtain a second captured image, the driving mode switching unit switches the driving mode to a second driving mode of long-time exposure in which a plurality of fields are combined to one field in a pseudo manner when the observation mode is the second observation mode, and the dimming controller causes each of the first light emitting element and the second light emitting element to emit light every entire line exposure period in which all lines in an effective pixel area in the image sensor are simultaneously exposed when the driving mode is the second driving mode, the entire line exposure period being a period generated in a pseudo manner by the second driving mode.

(9) A medical observation system including: an imaging device including a rolling shutter type image sensor in which a plurality of pixels are two-dimensionally arrayed in units of horizontal lines; a light source device including a light emitting element which emits light according to a supplied current; and a medical control device that controls operations of the imaging device and the light source device, in which the medical control device includes: a driving mode switching unit that switches a driving mode of the image sensor; and a dimming controller that controls the light emitting element, and the dimming controller switches control of the light emitting element according to the driving mode.

With a medical control device and a medical observation system according to the present disclosure, it is possible to generate an image suitable for observation.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical control device comprising:
a driving mode switch configured to switch a driving mode of a rolling shutter type image sensor in which a plurality of pixels are two-dimensionally arrayed in units of horizontal lines between a first driving mode that generates no single line exposure period in which all horizontal lines in an effective pixel area in the image sensor are simultaneously exposed and a second driving mode of long-time exposure in which a plurality of fields are combined to one field to generate a single line exposure period in which all horizontal lines in an effective pixel area in the image sensor are simultaneously exposed; and
a dimming controller configured to
control a light emitting element configured to emit light according to a supplied current, and
on condition that the driving mode is the first driving mode, adjust an electronic shutter of the image sensor during dimming control, or
on condition that the driving mode is the second driving mode, fix the electronic shutter of the image sensor during dimming control.

2. The medical control device according to claim 1, wherein the dimming controller is configured to:
execute dimming control including
first control for adjusting a supply time of a current to be supplied to the light emitting element,
second control for adjusting a current value to be supplied to the light emitting element, and
third control for adjusting an electronic shutter of the image sensor; and
switch the dimming control according to the driving mode.

3. The medical control device according to claim 2, wherein the dimming controller is configured to execute only the second control and the third control among the first to the third controls in a case where the driving mode is the first driving mode.

4. The medical control device according to claim 2, wherein the dimming controller is configured to execute only the first control and the second control among the first to the third controls in a case where the driving mode is the second driving mode.

5. The medical control device according to claim 4, wherein the dimming controller is configured to, when the driving mode is the second driving mode, set a light emission amount of the light emitting element in an exposure period in which all lines of an effective pixel area in the image sensor are simultaneously exposed to be higher than a light emission amount of the light emitting element in another period, the single line exposure period being generated in a pseudo manner by combining the exposure period and the another period by the second driving mode.

6. The medical control device according to claim 2, wherein the dimming controller is configured to execute only the first control and the second control among the first to the third controls in a case where the driving mode is a third driving mode including binning.

7. The medical control device according to claim 6, wherein the dimming controller is configured to, when the driving mode is the third driving mode, set a light emission amount of the light emitting element in an exposure period in which all lines of an effective pixel area in the image sensor are simultaneously exposed to be higher than a light emission amount of the light emitting element in another period, the single, line exposure period being a period generated in a pseudo manner by combining the exposure period and the another period by the third driving mode.

8. The medical control device according to claim 1, wherein
the light emitting element includes
a first light emitting element configured to emit light in a first wavelength band, and a second light emitting element configured to emit light in a second wavelength band different from the first wavelength band, the medical control device further comprises an observation mode switch configured to switch an observation mode between a first observation mode and a second observation mode, the first observation mode is an observation mode in which an observation target irradiated with the light in the first wavelength band is captured by the image sensor to obtain a first captured image, the second observation mode is an observation mode in which the first captured image is obtained and the observation target irradiated with the light in the second wavelength band is captured by the image sensor to obtain a second captured image, the driving mode switch is configured to switch the driving mode to the second driving mode when the observation mode is the second observation mode, and the dimming controller is configured to cause each of the first light emitting element and the second light emitting element to emit light every entire line exposure period in which all lines in an effective pixel area in the image sensor are simultaneously exposed when the driving mode is the second driving mode, the entire line exposure period being a period generated in a pseudo manner by the second driving mode.

9. A medical observation system comprising:

an imaging device including a rolling shutter type image sensor in which a plurality of pixels are two-dimensionally arrayed in units of horizontal lines;

a light source including a light emitting element configured to emit light according to a supplied current; and a medical controller configured to control operations of the imaging device and the light source, the medical controller including:

a driving mode switch configured to switch a driving mode of the image sensor between a first driving mode that generates no single line exposure period in which all horizontal lines in an effective pixel area in the image sensor are simultaneously exposed and a second driving mode of long-time exposure in which a plurality of fields are combined to one field to generate a single line exposure period in which all horizontal lines in an effective pixel area in the image sensor are simultaneously exposed; and a dimming controller configured to control the light emitting element, and on condition that the driving mode is the first driving mode, adjust an electronic shutter of the image sensor during dimming control, or on condition that the driving mode is the second driving mode, fix the electronic shutter of the image sensor during dimming control.

10. The medical observation system according to claim 9, wherein the dimming controller is configured to:

execute dimming control including first control for adjusting a supply time of a current to be supplied to the light emitting element, second control for adjusting a current value to be supplied to the light emitting element, and third control for adjusting an electronic shutter of the image sensor; and switch the dimming control according to the driving mode.

11. The medical observation system according to claim 10, wherein the dimming controller is configured to execute only the second control and the third control among the first to the third controls in a case where the driving mode is a first driving mode in which there is no single line exposure period in which all horizontal lines in an effective pixel area in the image sensor are simultaneously exposed.

12. The medical observation system according to claim 10, wherein the dimming controller is configured to execute only the first control and the second control among the first to the third controls in a case where the driving mode is the second driving mode.

13. The medical observation system according to claim 12, wherein the dimming controller is configured to, when the driving mode is the second driving mode, set a light emission amount of the light emitting element in an entire line exposure period in which all lines of an effective pixel area in the image sensor are simultaneously exposed to be higher than a light emission amount of the light emitting element in another period.

14. The medical observation system according to claim 10, wherein the dimming controller is configured to execute only the first control and the second control among the first to the third controls in a case where the driving mode is a third driving mode including binning.

15. The medical observation system according to claim 14, wherein the dimming controller is configured to, when the driving mode is the third driving mode, set a light emission amount of the light emitting element in an entire line exposure period in which all lines of an effective pixel area in the image sensor are simultaneously exposed to be higher than a light emission amount of the light emitting element in another period, the entire line exposure period being a period generated in a pseudo manner by the third driving mode.

16. The medical observation system according to claim 9, wherein the light emitting element is a first light emitting element configured to emit light in a first wavelength band, and the light source further includes a second light emitting element configured to emit light in a second wavelength band different from the first wavelength band, the medical controller further comprises an observation mode switch configured to switch an observation mode between a first observation mode and a second observation mode, the first observation mode is an observation mode in which an observation target irradiated with the light in the first wavelength band is captured by the image sensor to obtain a first captured image, the second observation mode is an observation mode in which the first captured image is obtained and the observation target irradiated with the light in the second wavelength band is captured by the image sensor to obtain a second captured image, the driving mode switch is configured to switch the driving mode to a second driving mode of long-time exposure in which a plurality of fields are combined to one field in a pseudo manner when the observation mode is the second observation mode, and the dimming controller is configured to cause each of the first light emitting element and the second light emitting element to emit light every entire line exposure period in which all lines in an effective pixel area in the image sensor are simultaneously exposed when the driving mode is the second driving mode, the entire line exposure period being a period generated in a pseudo manner by the second driving mode.

17. A medical observation method comprising:
switching a driving mode of a rolling shutter type image sensor in which a plurality of pixels are two-dimensionally arrayed in units of horizontal lines between a first driving mode that generates no single line exposure period in which all horizontal lines in an effective pixel area in the image sensor are simultaneously exposed and a second driving mode of long-time exposure in which a plurality of fields are combined to one field to generate a single line exposure period in which all horizontal lines in an effective pixel area in the image sensor are simultaneously exposed; and
controlling dimming by
controlling a light emitting element configured to emit light according to a supplied current, and
on condition that the driving mode is the first driving mode, adjusting an electronic shutter of the image sensor during dimming control, or
on condition that the driving mode is the second driving mode, fixing the electronic shutter of the image sensor during dimming control.

18. The medical observation method according to claim 17, wherein controlling dimming includes:
performing a first control for adjusting a supply time of a current to be supplied to the light emitting element,
performing a second control for adjusting a current value to be supplied to the light emitting element, and
performing a third control for adjusting an electronic shutter of the image sensor; and
switch the dimming control according to the driving mode.

19. The medical observation method according to claim 17, wherein controlling dimming includes performing only the second control and the third control among the first to the third controls in a case where the driving mode is a first driving mode in which there is no single line exposure period in which all horizontal lines in an effective pixel area in the image sensor are simultaneously exposed.

20. The medical observation method according to claim 17, wherein controlling dimming includes performing only the first control and the second control among the first to the third controls in a case where the driving mode is the second driving mode.

* * * * *